United States Patent [19]

Prugh

[11] Patent Number: 4,540,796

[45] Date of Patent: Sep. 10, 1985

[54] PROCESS FOR PREPARING INHIBITORS OF 3-HYDROXY-3-METHYLGLUTARYL COENZYME A REDUCTASE VIA A CHIRAL SYNTHON

[75] Inventor: John D. Prugh, Chalfont, Pa.

[73] Assignee: Merck & Co., Inc., Rahway, N.J.

[21] Appl. No.: 568,977

[22] Filed: Jan. 6, 1984

Related U.S. Application Data

[62] Division of Ser. No. 373,605, May 3, 1982, Pat. No. 4,440,927.

[51] Int. Cl.$^3$ ............................................ C07D 309/30

[52] U.S. Cl. ..................................................... 549/292
[58] Field of Search ......................................... 549/292

Primary Examiner—Norma S. Milestone
Attorney, Agent, or Firm—Joseph F. DiPrima; Michael C. Sudol

[57] ABSTRACT

Totally synthetic analogs of the known inhibitors of 3-hydroxy-3-methylglutaryl coenzyme A reductase, compactin and mevinolin, are prepared from a chiral synthon derived from D-glucose which has the same chirality as the natural products.

3 Claims, No Drawings

PROCESS FOR PREPARING INHIBITORS OF 3-HYDROXY-3-METHYLGLUTARYL COENZYME A REDUCTASE VIA A CHIRAL SYNTHON

This is a division of application Ser. No. 373,605, filed May 3, 1982, now U.S. Pat. No. 4,440,927, issued Apr. 3, 1984.

BACKGROUND OF THE INVENTION

This invention is concerned with a novel chiral synthesis of antihypercholesterolemic compounds which derive their utility from their ability to inhibit 3-hydroxy-3-methylglutaryl-coenzyme A reductase (HMG-CoA reductase) and have the structural formula:

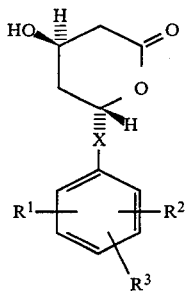

I

The chiral synthesis is accomplished through the use of a chiral synthon of structural formula:

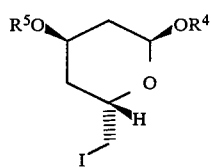

II with which this invention is also concerned.

Endo. et al., *J. Antibiotics*, XXIX, 1346 (1976) described a fermentation product, ML-236B, with potent antihyperchlolesterolemic activity which acts by inhibiting HMG-CoA reductase. This material, named compactin by Brown et al., *J. Chem. Soc., Perkin I,* 1165, (1965) was shown to have to have a desmethyl mevalonolactone partial structure and the stereochemistry was studied.

Shortly thereafter a chemically similar, natural product MK-803 (mevinolin), obtained by fermentation, was isolated and characterized, by Monaghan et al., U.S. Pat. No. 4,231,938. It has been shown to have the same desmethyl mevalonolactone partial structure and the absolute stereochemical configuration has been determined and described in EPO publication No. 0,022,478 of Merck & Co., Inc.

Totally synthetic analogs of structure I have been prepared and described in Sankyo's U.S. Pat. No. 4,198,425 and Sankyo's U.S. Pat. No. 4,255,444 with no attempt being made to separate the stereo- and optical isomers. Subsequently, as described in Merck's EPO publication No. 0,024,348 and by Meyer, *Ann. Chem.,* (1979), pages 484–491, similar totally synthetic analogs were separated into their stereoisomers and optical enantiomers. Furthermore, it was shown in EPO publication No. 0,024,348 that essentially all of the HMG-CoA reductase activity resides in the 4(R)-trans species as is the case with the naturally occurring compounds compactin and mevinolin.

In the prior art process for preparing the totally synthetic compounds, the lactone moiety of each compound has to be elaborated by a lengthy series of synthetic operations followed by very tedious and expensive chromatographic separation of the cis, trans racemates, and optical resolution of the trans racemate to afford the dextrorotatory enantiomer.

Now, with the present invention, there is available a novel chiral synthon which, after reaction with a second intermediate, representing the aryl moiety, and removal of protecting groups, provides the product of structure I with the desired chirality directly.

DETAILED DESCRIPTION OF THE INVENTION

This invention is concerned with a chiral synthon of structural formula II:

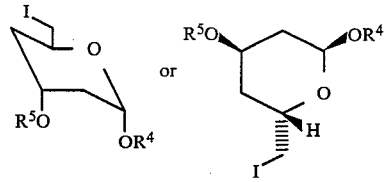

where $R^4$ is $C_{1-3}$ alkyl, preferably methyl; and $R^5$ is benzyl, or 4-methoxybenzyl, preferably benzyl.

The synthon is prepared in a multistep process starting with $C_{1-3}$ alkyl 4,6-benzylidene-2-deoxy-α-D-ribohexopyranoside, the final step of which comprises substitution of an iodo group for a sulfonyloxy group on the 6-carbon of a methyl pyranoside, depicted as follows:

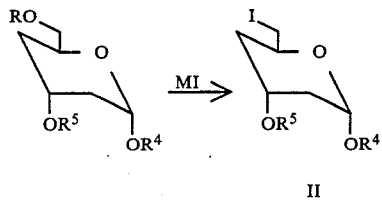

II wherein R is methanesulfonyl, ethanesulfonyl, benzenesulfonyl, or o, m or p-toluenesulfonyl, preferably the latter, and MI is an alkali metal iodide, preferably potassium or sodium iodide.

The reaction is conducted in a polar anhydrous solvent such as acetone, methyl ethyl ketone, dimethylsulfoxide, dimethylformamide, or the like, by heating at about 50° to about 100° C. for about 10 to about 48 hours. The reaction is best conducted in the absence of oxygen and light.

This invention is also concerned with a novel process for utilizing the novel, chiral synthon in the synthesis of HMG-CoA reductase inhibitors which is represented by the following reactions of Flow Sheets I and II:

FLOW SHEET I
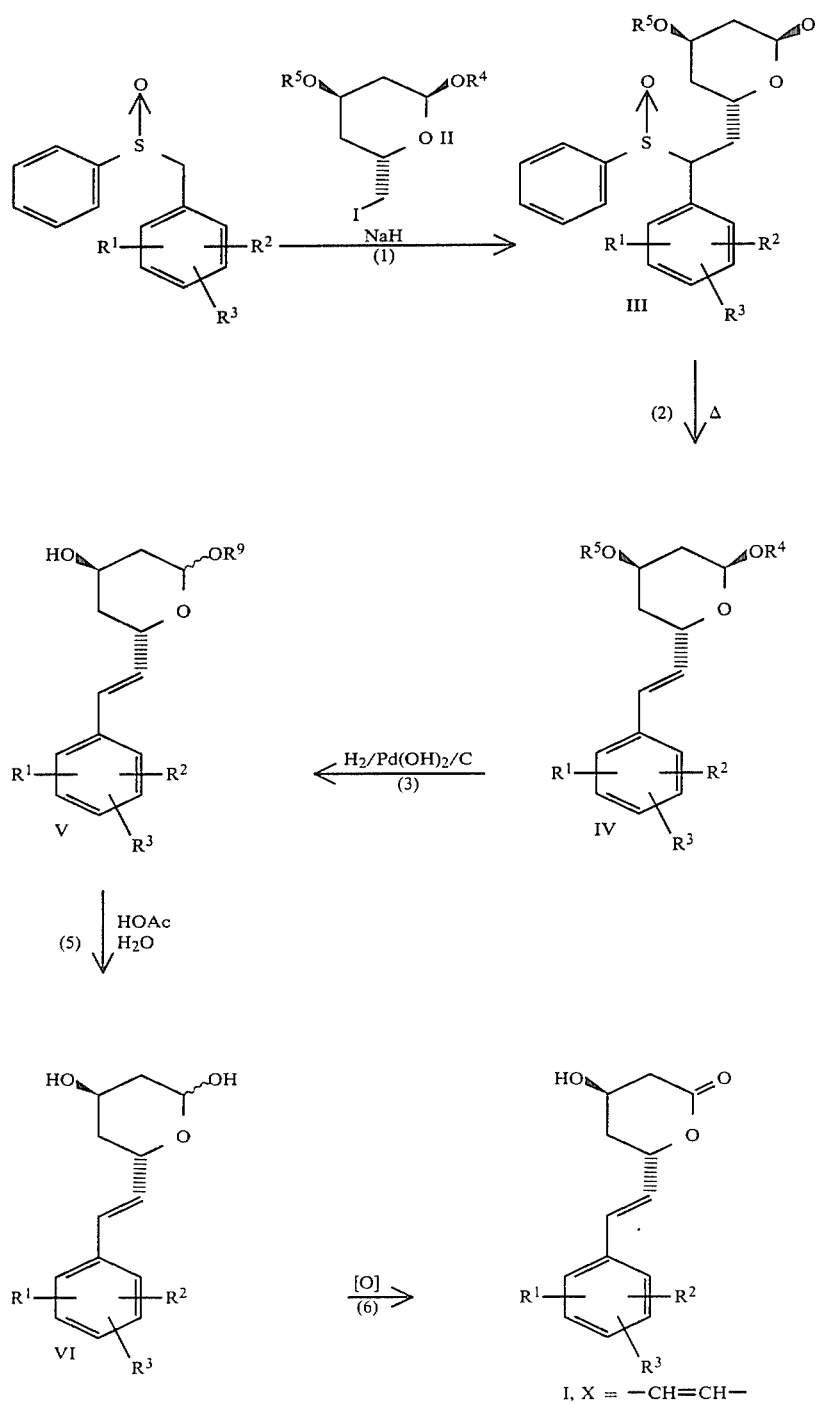

FLOW SHEET II
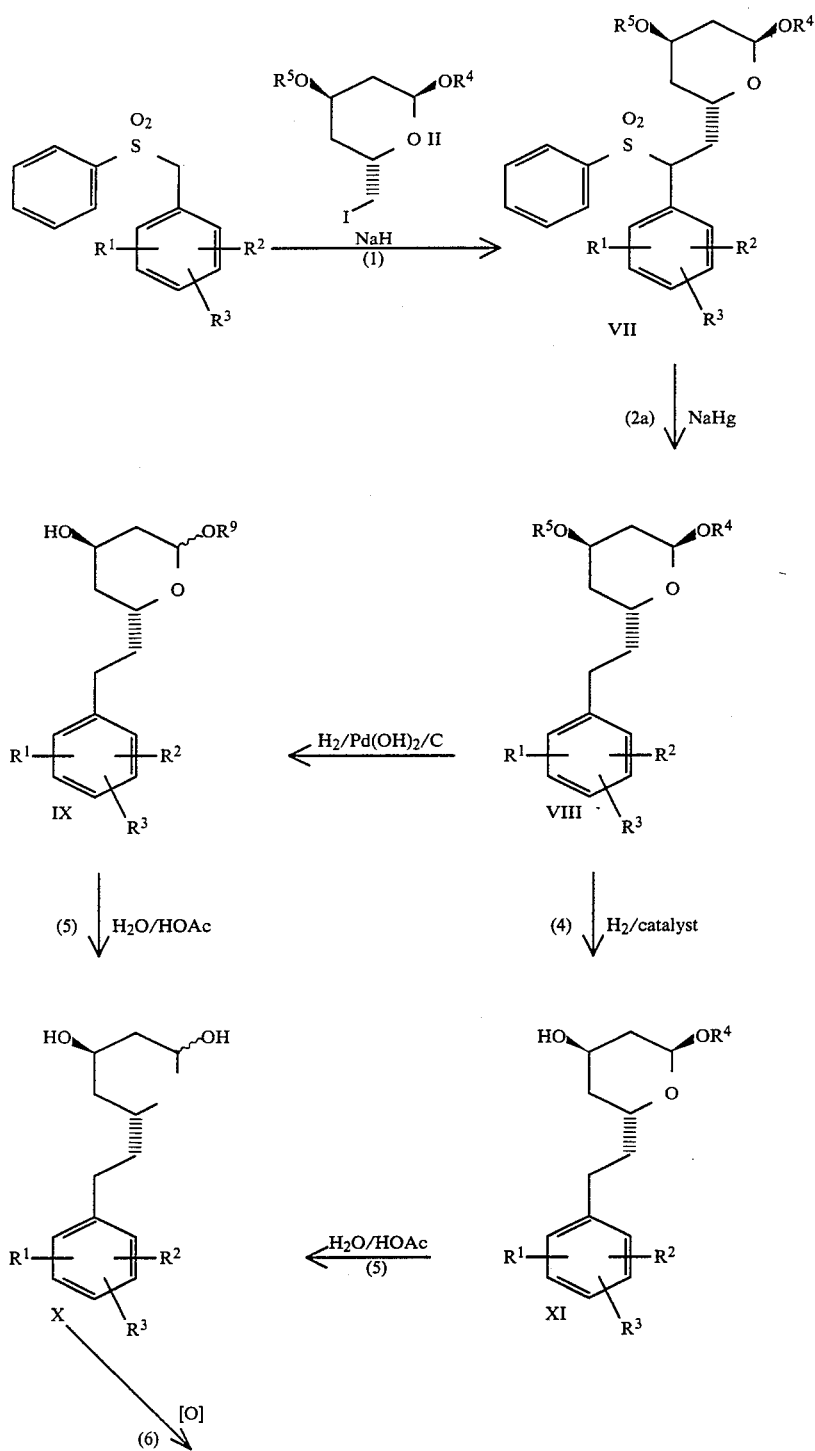

FLOW SHEET II
-continued

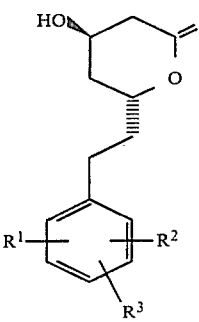

I, X = —CH$_2$CH$_2$—

In the foregoing Flow Sheets:
R$^2$ and R$^3$ are independently chloro, or C$_{1-3}$ alkyl, preferably methyl and are preferably on the 2- and 4-positions respectively;
R$^1$ is preferably in the 6-position and is

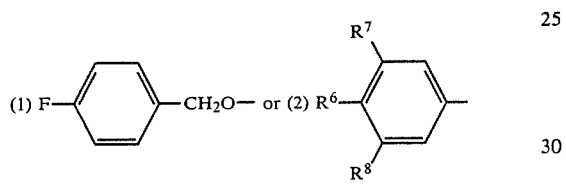

R$^6$ is hydrogen, fluoro or chloro and
R$^7$ and R$^8$ are independently hydrogen, chloro, or C$_{1-3}$alkyl, preferably methyl,
and R$^4$ and R$^5$ are as previously defined.

Reagents and Reaction Conditions:

(1) A mixture of the sulfoxide or sulfone in dimethylformamide, dimethyl sulfoxide, N-methylpyrrolidone, or the like and NaH is stirred at about 20°–80° C. until hydrogen evolution ceases (0.25 to about 2 hours). The synthon in the same solvent is added and stirring continued another 1–4 hours.

(2) Compound III in benzene, toluene, xylene, or other liquid aromatic hydrocarbon is heated at about 45°–80° C. for 2 to about 12 hours in the presence of a suitable base such as sodium or potassium carbonate.

(2a) Compound VII in a C$_{1-3}$ alkanol, in the presence of 1–3 molar excess of Na$_2$HPO$_4$ is treated with sodium amalgam at 20° to about 40° C. for 0.25 to about 6 hours.

(3) Compound IV or VIII in a C$_{2-4}$ alkanol of formula R$^9$OH, preferably ethanol is treated with 20% palladium hydroxide on carbon (Pearlman catalyst) at about 75° to about 125° C. until the reaction is substantially complete in 0.5 to 5 days.

(4) Compound VIII in a C$_{1-3}$ alkanol is stirred at 20°–40° C. under 1 to 2 atmospheres of hydrogen pressure in the presence of a noble metal hydrogenation catalyst such as Pd/C or Pd until 1 mole of hydrogen is consumed per mole of starting material.

(5) Compound V, IX or XI is treated with aqueous acetic acid at 15° C. to about 80° C. until the reaction is substantially complete in about 2 to about 36 hours, depending on the temperature employed.

(6) Compound VI or X in an inert solvent such as benzene, toluene, methylene chloride, or tetrachloroethylene is treated with a suitable oxidizing agent such as N-iodosuccinimide-tetra-n-butylammonium iodide, silver oxide, silver carbonate/Celite, sodium hypoiodite or the like, at about 20°–40° C. for 1 to about 8 hours.

An essential part of the novel synthesis of this invention is the group of benzyl sulfoxides and sulfones which are reacted with the novel synthon of this invention. They are prepared from the corresponding substituted benzaldehydes in accordance with the reaction sequences shown in Flow Sheet III. The starting aldehydes are prepared as described in EP publication No. 0 024 348 of Merck & Co., Inc.

FLOW SHEET III

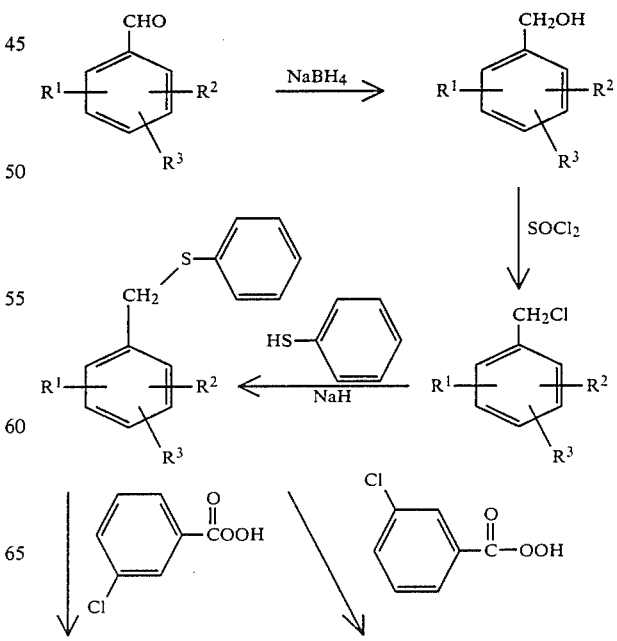

-continued
FLOW SHEET III

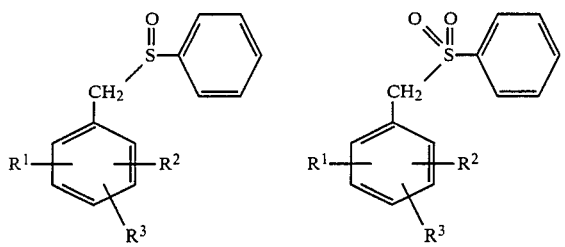

These syntheses are illustrated by the following preparations of: (A) (4'-fluoro-3,3',5-trimethyl[1,1'-biphenyl]-2-yl-methyl)phenyl sulfoxide; and (B) the corresponding sulfone.

(A) 1. 4'-Fluoro-2-hydroxymethyl-3,3',5-trimethyl-1,1'-biphenyl.

Sodium borohydride (0.45 g, 12 mmoles) was added to a stirred suspension of 4'-fluoro-3,3',5-trimethyl-1,1'-biphenyl-2-carboxaldehyde (2.9 g, 12 mmoles) in ethanol (20 ml) which was cooled in an ice-water bath. After 5 minutes the cooling bath was removed and the reaction mixture was stirred at ambient temperature for one hour. The solution was cooled to 0° C. and excess ammonium chloride (2.67 g, 50 mmoles) was added and the mixture was partitioned between ether (150 ml) and water (50 ml). The water was separated and extracted with ether (50 ml). The combined ether extracts were washed with water (2×50 ml) dried (MgSO4), filtered, and the solvent evaporated in vacuo to leave the title compound, a gum which crystallized on standing, to give 2.77 g, m.p. 74°–75° C. A sublimed sample had m.p. 102°–103° C.

(A) 2. 2-Chloromethyl-4'-fluoro-3,3',5-trimethyl-1,1'-biphenyl

4'-Fluoro-2-hydroxymethyl-3,3',5-trimethyl-1,1'-biphenyl (2.77 g, 11.3 mmoles) was added in divided portions to thionyl chloride (10 ml) and then heated with stirring in an 80° bath for one hour. The reaction was then diluted with 50 ml of dry toluene and the solvent was evaporated in vacuo to leave 3.27 g of the title compound.

(A) 3. (4'-Fluoro-3,3',5-trimethyl-[1,1'-biphenyl]-2-yl-methyl)phenyl sulfide

Thiophenol (1.4 ml, 13.6 mmoles) was added dropwise to a stirred suspension of sodium hydride (0.653 g, 13.6 mmoles) in dry DMF under an atmosphere of nitrogen. The mixture was then heated at 50° C. for 30 minutes until all of the sodium hydride was consumed and hydrogen evolution ceased. To this solution was added a solution of 2-chloromethyl-4'-fluoro-3,3',5-trimethyl-1,1'-biphenyl (3.27 g crude, approximately 11.3 mmoles) in 8 ml of dry DMF and the mixture was heated at 50° with stirring for 30 minutes. The reaction was cooled to room temperature and partitioned between ether (200 ml) and dilute sodium hydroxide solution (50 ml). The ether solution was extracted with dilute sodium hydroxide solution (50 ml) again, then extracted with dilute sodium chloride solution (2×100 ml). The ether solution was then dried (MgSO4), filtered, and the solvent was evaporated to leave 3.75 g of product. This material was purified by flash chromatography on silica gel with a 60×150 mm column eluting with methylene chloride/hexane, ¼ (v:v) to give 3.1 g of the title compound, m.p. 72°–74° C.

(A) 4. (4'-Fluoro-3,3',5-trimethyl-[1,1'-biphenyl]-2-yl-methyl)phenyl sulfoxide m-Chloroperbenzoic acid (tech. grade, approximately 75% peroxide; 1.19 g, approximately 5 mmoles) was added in small portions to a stirred solution of (4'-fluoro-3,3',5-trimethyl-[1,1'-biphenyl]-2-yl-methyl)-phenyl sulfide (1.68 g, 5 mmoles) at −78° C. The reaction mixture was then stirred at −78° C. for 30 minutes and allowed to warm to room temperature. The solution of the product was separated by filtration from the 3-chlorobenzoic acid which was washed with methylene chloride. The combined methylene chloride solutions of the product were diluted with methylene chloride to 100 ml then washed with dilute sodium hydroxide solution (2×50 ml) dried (MgSO4), filtered, and the solvent was evaporated in vacuo to leave 1.7 g of crude product. This was purified by flash chromatography on silica gel using a 40×150 mm column eluting with 3.5% (v:v) acetone in methylene chloride to give 1.55 g of the title compound as a gum. Dry toluene was added and evaporated in vacuo four times to dry the product, which then crystallized, m.p. 75°–85° C. Cald'd for $C_{22}H_{21}FSO$: C, 74.97; H, 6.01 Found: C, 75.01, H, 6.19.

(B) (4'-Fluoro-3,3',5-trimethyl-[1,1'-biphenyl]-2-yl-methyl)phenyl sulfone m-Chloroperbenzoic acid (tech. grade, approximately 75% peroxide; 2.38 g, approximately 10 mmoles) is added in small portions to a stirred solution of (4'-fluoro-3,3',5-trimethyl-[1,1'-biphenyl]-2-yl-methyl)phenyl sulfide (1.68 g, 5 mmoles) in chloroform (40 ml) at −5° C. and the mixture is stirred at ambient temperature overnight. The reaction is then refluxed with stirring for 3 hours, cooled to room temperature, and filtered to remove the insoluble m-chlorobenzoic acid. The acid is washed with chloroform. The combined chloroform filtrate and washings are washed with dilute sodium hydroxide solution, dried (MgSO4), filtered and the solvent is evaporated in vacuo to give the crude product. This material is purified by flash chromatography on a 40×150 mm column eluting with 1% (v:v) acetone in methylene chloride to give the title compound.

Employing the procedures substantially as outlined above, the following benzyl sulfoxides and sulfones are prepared:

| 6-$R^1$ | 2-$R^2$ | 4-$R^3$ | n |
|---|---|---|---|
| H | Cl | Cl | 1 |
| H | Cl | Cl | 2 |
| F—⟨⟩— | Cl | Cl | 1 |
| F—⟨⟩—CH3 | Cl | Cl | 1 |

-continued

| 6-R¹ | 2-R² | 4-R³ | n |
|---|---|---|---|
| (2,6-dichlorophenyl: Cl, Cl) | CH₃ | CH₃ | 1 |
| (4-F-phenyl) | CH₃ | CH₃ | 1 |
| (2-F, 6-CH₃-phenyl) | Cl | CH₃ | 1 |
| (2-F, 4,6-di-CH₃-phenyl) | CH₃ | CH₃ | 1 |
| (3,5-di-CH₃-phenyl) | Cl | Cl | 1 |
| (3,5-di-CH₃-phenyl) | CH₃ | CH₃ | 1 |
| F—⟨phenyl⟩—CH₂O | CH₃ | CH₃ | 1 |
| F—⟨phenyl⟩—CH₃O | Cl | Cl | 1 |
| F—⟨phenyl⟩ | Cl | Cl | 2 |
| (2-F, 6-CH₃-phenyl) | Cl | Cl | 2 |
| (2,6-dichlorophenyl) | CH₃ | CH₃ | 2 |
| F—⟨phenyl⟩ | CH₃ | CH₃ | 2 |
| (2-F, 6-CH₃-phenyl) | Cl | CH₃ | 2 |

-continued

| 6-R¹ | 2-R² | 4-R³ | n |
|---|---|---|---|
| (2-F, 6-CH₃, and CH₃-phenyl) | CH₃ | CH₃ | 2 |
| (3,5-di-CH₃-phenyl) | Cl | Cl | 2 |
| (3-CH₃-phenyl) | CH₃ | CH₃ | 2 |
| F—⟨phenyl⟩—CH₂O | CH₃ | CH₃ | 2 |
| F—⟨phenyl⟩—CH₂O | Cl | Cl | 2 |

The preparation of the novel chiral synthon starts with a known carbohydrate derivative, having the desired chirality, and is described fully in the Example that follows.

EXAMPLE I

The Synthon

Methyl 3-O-benzyl-6-iodo-2,4,6-tri-deoxy-α-D-erythrohexopyanoside
or
(2R,4R,6S)-4-benzyloxy-6-iodomethyl-2-methoxy-3,4,5,6-tetrahydro-2H-pyran
or
Methyl 3-O-benzyl-6-iodo-2,4,6-trideoxy-α-D-allopyranoside Step A: Preparation of methyl 3-O-benzyl-4,6-O-benzylidene 2-deoxy-α-D-ribo-hexopyranoside (2)

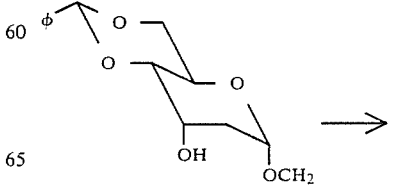

1

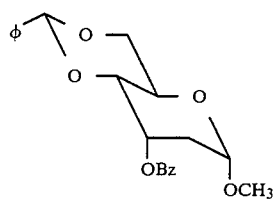

2

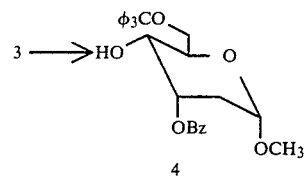

4

Methyl 4,6-benzylidene-2-deoxy-α-D-hexopyranoside (53.25 g; 0.2 mol) was dissolved in dry DMF (400 ml). Sodium-hydride, (50% in mineral oil, 10.56 g; 0.22 mole) was added and stirred vigorously under nitrogen for 40 minutes. Benzyl bromide (37.63 g; 0.22 mole) was added dropwise over a period of 25 minutes and the reaction temperature was maintained below 40° C. with occasional cooling in an ice bath. The reaction was stirred at 40° C. for an additional 30 minutes. The reaction was cooled to room temperature and poured into 1200 ml of ice water, seeded and triturated until a solid was deposited. The solid was collected, washed with water and dried in a vacuum oven at 60° C. under a slow stream of air overnight to give 73.12 g of product which was recrystallized from hexane to give 65.14 g of methyl 3-O-benzyl-4,6-O-benzylidene-2deoxy-α-D-ribo-hexopyranoside; m.p. 95°–96° C.; $[\alpha]_D^{25} = 58.56°$ (c,0.7, CHCl$_3$).

Calc. for C$_{21}$H$_{24}$O$_5$: C, 70.77; H, 6.79. Found: C, 70.75; H, 6.81.

Step B: Preparation of Methyl 3-O-benzyl-2-deoxy-α-D-ribo-hexopyranoside (3)

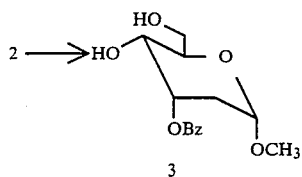

3

Methyl 3-O-benzyl-4,6-O-benzylidene-2-deoxy-α-D-ribo-hexopyranoside (7.2 g; 20 mmoles) was dissolved in methylene chloride (100 ml). Aqueous trifluoroacetic acid (70% TFA in water; 4.8 ml) was added with vigorous stirring. The reaction was stirred vigorously for 10 minutes and immediately quenched by adding 20 ml of saturated aqueous sodium carbonate solution with vigorous stirring. The methylene chloride layer was separated and the aqueous layer was extracted with methylene chloride. The combined methylene chloride extracts were dried (K$_2$CO$_3$), filtered, and the solvent was evaporated in vacuo to give the crude product, which was chromatographed on 500 g of silica gel eluting with 15% (by volume) acetone in methylene chloride for 2 L, then 20% acetone in methylene chloride thereafter. Fractions containing the product (visualized on silica gel tlc plate with 7% phosphomolybdic acid in ethanol followed by heat) were collected and evaporated in vacuo to leave 4.96 g of methyl 3-O-benzyl-2-deoxy-α-D-ribo-hexopyranoside as a glassy oil, $[\alpha]_D^{25} = +170.58$ (c, 0.2, CHCl$_3$).

Calc. for C$_{14}$H$_{20}$O$_5$·½H$_2$O: C, 60.70; H, 7.63. Found: C, 60.78; H, 7.38.

Step C: Preparation of Methyl 3-O-benzyl-6-O-trityl-2-deoxy-α-D-ribo-hexopyranoside (4)

Methyl 3-O-benzyl-2-deoxy-α-D-ribo-hexopyranoside (4.6 g; 17.9 mmoles) was dissolved in dry pyridine (50 ml). Triphenylmethyl chloride (5.24 g; 18.8 mmoles) was added and the solution was stirred for 6 days under nitrogen. Water (400 ml) and saturated aqueous sodium bicarbonate were added and the pyridine was removed azeotropically in vacuo. The product was extracted with ether, dried (K$_2$CO$_3$, anhyd) and evaporated in vacuo to leave 10.0 g of product which was chromatographed on 500 g silica gel, eluting with 1.5 L of methylene chloride followed by 5% (by volume) acetone in methylene chloride. Fractions containing the product were collected to give 7.9 g of methyl 3-O-benzyl-6-O-trityl-2-deoxy-α-D-ribo-hexopyranoside, as a gum,- $[\alpha]_D^{25} = 87.23°$(C, 0.35, CHCl$_3$)

Calc. for C$_{33}$H$_{34}$O$_5$: C, 77.62; H, 6.71. Found: C, 77.38; H, 6.76.

Step D: Preparation of Methyl 3-O-benzyl-4-O-tosyl-6-O-trityl-2-deoxy-α-D-ribo-hexopyranoside (5)

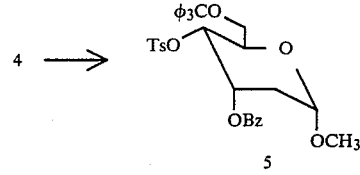

5

Methyl 3-O-benzyl-6-O-trityl-2-deoxy-α-D-ribo-hexopyranoside (13.3 g; 26.05 mmoles) was dissolved in dry pyridine (41 ml) and cooled in an ice bath under nitrogen. p-Toluenesulfonyl chloride (9.93 g, 52.09 mmoles) was added all at once and the reaction was stirred at room temperature under nitrogen overnight. The reaction was partitioned between ether and water. The ether layer was extracted four times with water, dried (K$_2$CO$_3$, anhyd), and the solvent evaporated in vacuo to leave 19.1 g of crude product which was chromatographed on silica gel (1 kg) eluting with methylene chloride until excess p-toluenesulfonyl chloride had been eluted. Elution was continued with 2% (by volume) acetone in methylene chloride. Fractions containing the product were collected and evaporated to dryness to leave 15.5 g of methyl 3-O-benzyl-4-O-tosyl-6-O-trityl-2-deoxy-α-D-ribo-hexopyranoside as a glassy gum, $[\alpha]_D^{25} = 66.24$ (C, 1.0, CHCL$_3$).

Calc. for C$_{40}$H$_{40}$O$_7$S: C, 72.27; H, 6.06. Found: C, 71.94; H, 6.32.

Step E: Preparation of Methyl 3-O-benzyl-4-O-tosyl-2-deoxy-α-D-ribo-hexopyranoside (6)

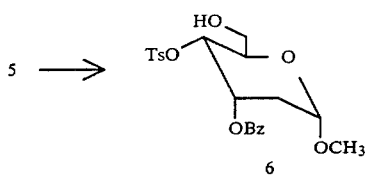

Methyl 3-O-benzyl-4-O-tosyl-6-O-trityl-2-deoxy-α-D-ribo-hexopyranoside (15.3 g; 23.01 mmoles) was dissolved in methylene chloride (200 ml). Aqueous trifluoroacetic acid (70% TFA in water, 9.6 ml) was added with vigorous stirring. The vigorous stirring was continued for five minutes (bright yellow color appears), then the reaction was quenched by the addition of saturated aqueous sodium carbonate solution (40 ml) with vigorous stirring (note: the reaction becomes colorless). The methylene chloride layer was separated and the aqueous layer extracted with methylene chloride. The combined methylene chloride extracts were dried (MgSO₄), filtered and the solvent was evaporated in vacuo to give crude product. This product was chromatographed on 650 g of silica gel eluting with 3 L of methylene chloride to remove triphenyl carbinol from the column followed by elution with 10% (by volume) acetone in methylene chloride. When a faintly visible opaque band of product neared the bottom of the column the fractions containing the product were collected and the solvent was evaporated in vacuo to leave 8.1 g of methyl 3-O-benzyl-4-O-tosyl-2-deoxy-α-D-ribo-hexopyranoside, m.p. 100°–101° C., $[\alpha]_D^{25} = 115.07$ (c, 0.48, CHCl₃)

Calc. for $C_{21}H_{26}O_7S$: C, 59.70; H, 6.20. Found: C, 60.09; H, 6.37.

Alternate Procedure for Steps C, D and E Combined: Preparation of Methyl 3-O-benzyl-4-O-tosyl-2-deoxy-α-D-ribohexopyranoside

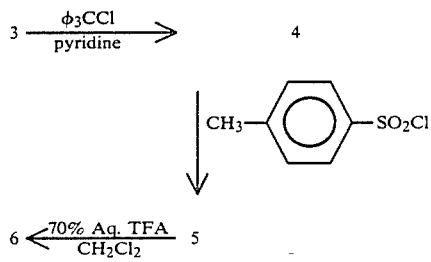

To a solution of methyl 3-O-benzyl-2-deoxy-α-D-ribo-hexopyranoside (6.0 g, 23.41 mmoles) in dry pyridine (65 mL) was added triphenylmethyl chloride (6.85 g, 24.58 mmoles). The resulting solution was stirred at room temperature under nitrogen for 48 hours. p-Toluenesulfonyl chloride (8.93 g, 46.82 mmoles) was added to the reaction mixture and stirring at room temperature under nitrogen was continued for 24 hours. The reaction was cooled in an ice bath and water (10 mL) was added dropwise. The ice bath was removed and the reaction mixture was stirred at ambient temperature for 1 hour. The reaction mixture was then dissolved in ether and the solution extracted with water four times. The ether phase containing the product was placed in a 3 L one-neck flask together with saturated sodium bicarbonate solution (50 mL) and water (100 mL). The ether and the pyridine/water azeotrope were removed in vacuo. The remaining gum was dissolved in ether, dried (MgSO₄), filtered and evaporated in vacuo to leave 15.0 g of crude methyl 3-O-benzyl-4-O-tosyl-6-O-trityl-2-deoxy-α-D-ribo-hexopyranoside. This material was dissolved in methylene chloride (200 mL). Trifluoroacetic acid (70% TFA in water, 9.6 mL) was added with vigorous stirring at room temperature. The vigorous stirring was continued for five minutes, then the reaction was quenched by the addition of saturated aqueous sodium carbonate solution (40 mL) with vigorous stirring. The reaction was now colorless. The methylene chloride layer was separated and the aqueous layer extracted with methylene chloride. The combined methylene chloride extracts were dried (MgSO₄), filtered and evaporated in vacuo to give the crude product. This product was chromatographed on 650 g of silica gel (EM Reag. 70–230 mesh) eluting with 3 L of methylene chloride to remove the triphenyl carbinol, followed by elution with 10% acetone in methylene chloride. Collection of fractions was begun when the faintly-visible opaque band of product neared the bottom of the column. The fractions containing the product were combined and the solvent evaporated in vacuo to leave 7.4 g (74.8% for the three steps) of product, 6, mp 94°–97° C.

Step F: Preparation of Methyl 3-O-benzyl-2,4-dideoxy-α-D-erythro-hexopyranoside (7)

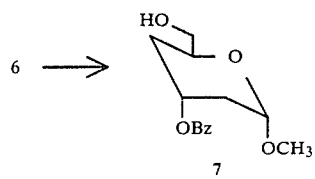

Methyl 3-O-benzyl-4-O-tosyl-2-deoxy-α-D-ribohexopyranoside (6.55 g, 15.50 mmoles) is dissolved in dry DMSO (50 ml). Sodium borohydride (2.35 g; 62.01 mmoles) is added and the reaction is stirred under nitrogen in a bath maintained at 80° C. for four days. The reaction is cooled to room temperature and diluted with ether and extracted with water. The aqueous extract is then extracted four times with ether. The combined ether extracts are dried (MgSO₄), filtered, and the solvent evaporated in vacuo to give crude product. This crude product is purified by flash chromatography on a 60 mm × 150 mm column eluting with 15% (by volume) acetone in methylene chloride. A small portion (0.9 g) containing an impurity is rechromatographed on a 30 mm × 130 mm column with the same eluant to give a combined total of 3.18 g of methyl 3-O-benzyl-2,4-dideoxy-α-D-erythro-hexopyranoside as a gum, $[\alpha]_D^{25}$ +58.56 (c, 0.7, CHCl₃)

Calc for $C_{14}H_{20}O_4$: C, 66.65; H, 7.97. Found: C, 66.66; H, 8.06.

Step G: Preparation of Methyl 3-O-benzyl-6-O-tosyl-2,4-dideoxy-α-D-erythro-hexopyranoside (8)

Methyl 3-O-benzyl-2,4-dideoxy-α-D-erythro-hexopyranoside (2.5 g; 9.91 mmoles) is dissolved in dry pyridine (20 ml) under nitrogen. p-Toluene-sulfonyl chloride (3.78 g; 19.8 mmoles) is added all at once and the reaction solution is stirred at room temperature for four hours. Water (5 ml) is added dropwise with stirring. A slight exotherm ensues; stirring is continued for one hour at ambient temperature. The reaction mixture is dissolved in ether and extracted successively with water (three times), dilute aqueous hydrochloric acid (twice), water and saturated aqueous sodium bicarbonate. The ether is dried (MgSO$_4$), filtered and the solvent evaporated in vacuo to leave 3.0 g of product which is purified by flash chromatography on silica gel on a 60 mm×150 mm column. Elution with 2% (by volume) acetone in methylene chloride gives 3.0 g of methyl 3-O-benzyl-6-O-tosyl-2,4-dideoxy-α-D-erythro-hexopyranoside, as a gum, $[\alpha]_D^{25} = 22.80$ (c, 1.2, CHCl$_3$)

Calc. for C$_{21}$H$_{26}$O$_5$S.H$_2$O: C, 61.74; H, 6.91. Found: C, 61.50; H, 6.55.

Step H: Preparation of Methyl 3-O-benzyl-6-iodo-2,4,6-tri-deoxy-α-D-erythro-hexopyranoside (9)

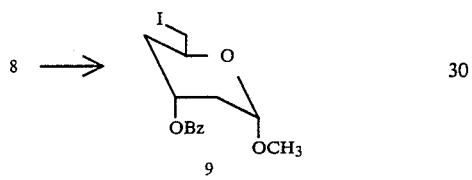

Methyl 3-O-benzyl-6-O-tosyl-2,4-dideoxy-α-D-erythro-hexopyranoside (3.0 g; 7.34 mmoles) and sodium iodide (13 g; 86.7 mmoles) are dissolved in acetone (130 ml). The resulting solution is refluxed under nitrogen and protected from the light for 24 hours. When tlc shows the reaction is complete (fluorosilica-methylene chloride, visualization with phosphomolybdic acid and heat), the acetone is evaporated in vacuo. The residue is partitioned between ether and water. The ether layer is washed with dilute aqueous sodium thiosulfate, then twice with water, dried (MgSO$_4$), filtered, and the solvent is evaporated in vacuo to give crude product which is purified by flash chromatography on silica gel on a 60 mm×150 mm column. Elution with methylene chloride gives 2.0 g of methyl 3-O-benzyl-6-iodo-2,4,6-trideoxy-α-D-erythro-hexopyranoside. $[\alpha]_D^{24}$ +53.45 (c, 0.66 CHCl$_3$). Pmr (300 MHz) (DCCl$_3$) δ1.52 (1H, m); 1.75 (1H, m); 1.95 (1H, m) 2.02 (1H, m); 3.21 (2H, m); 3.47 (3H, s); 3.78 (1H, m) 4.10 (1H, m); 4.56 (2H, q); 4.81 (1H, d); 7.24–7.42 (5H, m).

EXAMPLE 2

(2S,4R,6S)-(E)-6-[2-(4'-fluoro-3,3',5-trimethyl[1,1'-biphenyl]-2-yl)ethenyl]-4-benzyloxy-3,4,5,6-tetrahydro-2-methoxy-2H-pyran Step A: Preparation of (2S,4R,6S)-1-(4'-Fluoro-3,3',5-trimethyl[1,1'-biphenyl]-2-yl)-2-(4-benzyloxy-3,4,5,6-tetrahydro-2-methoxy-2H-pyran-6-yl)-1-ethyl(phenyl)sulfoxide

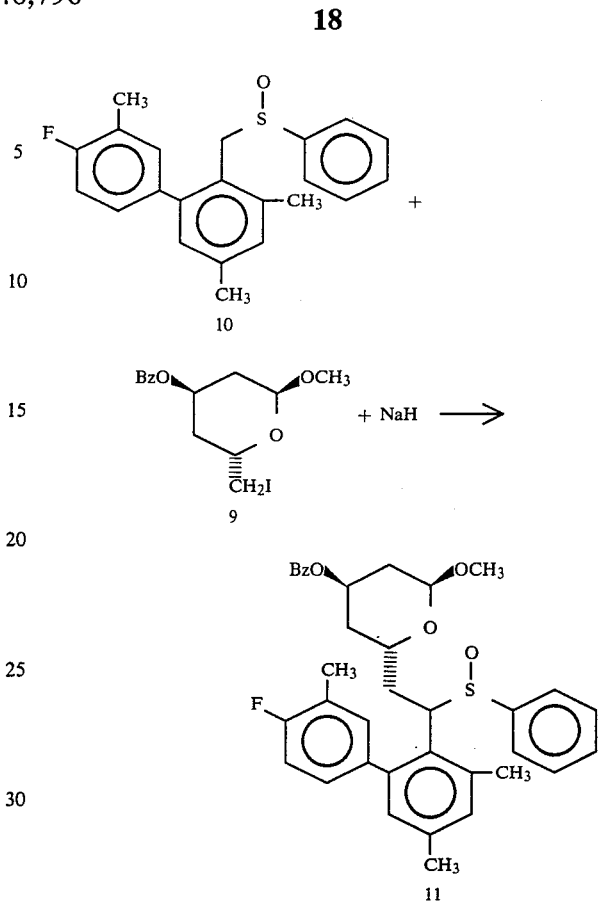

Sodium hydride (0.030 g, 0.63 mmoles) was suspended in dry DMSO (0.5 mL) under nitrogen and heated at 60°–70° C. for 1 hour until hydrogen evolution ceased and then cooled to room temperature. A solution of (4'-fluoro-3,3',5-trimethyl[1,1'-biphenyl]-2-yl)methyl(phenyl)sulfoxide (0.211 g, 0.60 mmoles) in dry DMSO (0.6 mL) was added by syringe through a septum and stirring was continued for 10 minutes. A solution of (2S,4R,6S)-4-benzyloxy-3,4,5,6-tetrahydro-6-iodomethyl-2-methoxy-2H-pyran (0.109 g, 0.3 mmole) in dry DMSO (0.6 mL) was added dropwise while the reaction mixture was stirred and cooled in an ice-water bath. After the addition was complete, the ice bath was removed and the reaction mixture was stirred at ambient temperature for one hour. The reaction mixture was then partitioned between ether (50 mL) and water (25 mL). The aqueous layer was extracted with ether and the combined ether extracts, washed with water (25 mL), dried (MgSO$_4$), filtered and evaporated in vacuo to leave 0.3 g of crude product mixture. Flash chromatography was carried out on a 20×150 mm column eluting with 2% acetone in methylene chloride (20 fractions of 10 mL each), then 5% acetone in methylene chloride (30 fractions of 10 mL each). The fractions containing the desired isomers of the product were combined and evaporated in vacuo to leave 68.9 mg of product as an isomer mixture (38% based on the synthon). This product is used without further purification in the next step.

Step B: Preparation of (2S,4R,6S)-(E)-6-[2-(4'-fluoro-3,3',5-trimethyl[1,1'-biphenyl]-2-yl)ethenyl]-4-benzyloxy-3,4,5,6-tetrahydro-2-methoxy-2H-pyran

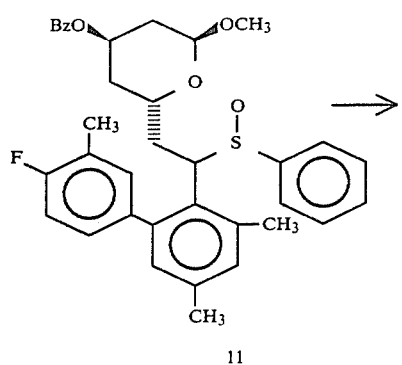

11

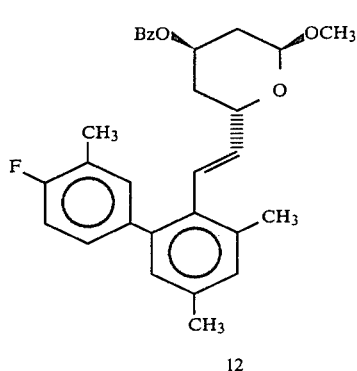

12

A suspension of (2S,4R,6S)-1-(4'-fluoro-3,3',5-trimethyl[1,1'-biphenyl]-2-yl)-2-[4-benzyloxy-3,4,5,6-tetrahydro-2-methoxy-2H-pyran-6-yl]-1-ethyl(phenyl)sulfoxide (62.9 mg, 0.107 mmole) and anhydrous potassium carbonate (100 mg, 0.724 mmole) in dry toluene (6 mL) was stirred and warmed in a heating bath at 90° C. for three hours. The reaction mixture was cooled to room temperature and the solvent evaporated in vacuo. The residue was repeatedly (5 times) warmed and triturated with a small amount of methylene chloride and then filtered through a tightly packed plug of glass wool. The solvent was then evaporated in vacuo. The crude product was purified by flash chromatography on a 10×150 mm column eluting with methylene chloride (10 fractions, 5 mL each), followed by 2% acetone in methylene chloride ( fractions, 5 mL each). The fractions containing the desired product were collected and evaporated to leave 35.8 mg of product as a gum (72.5%).

$[\alpha]_D^{24}$ +62.72 (c, 0.59, CHCl$_3$).

Calc'd for C$_{30}$H$_{33}$FO$_3$: C, 78.23; H, 7.22. Found: C, 78.37; H, 7.40.

Step C: Preparation of (4R,6S)-(E)-6-[2-(4'-Fluoro-3,3',5-trimethyl[1,1'-biphenyl]-2-yl)ethenyl]-2-ethoxy-3,4,5,6-tetrahydro-4-hydroxy-2H-pyran

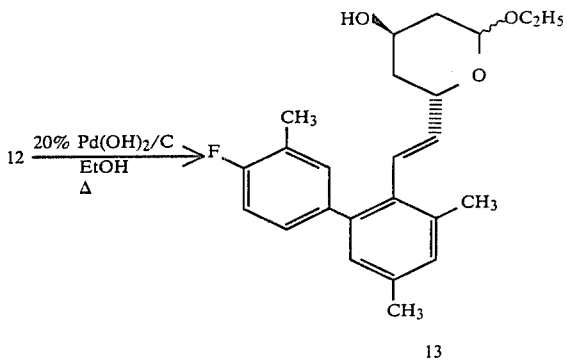

13

To a solution of (2S,4R,6S)-(E)-6-[2-(4'-fluoro-3,3',5-trimethyl[1,1'-biphenyl]-2-yl)ethenyl]-4-benzyloxy-3,4,5,6-tetrahydro-2-methoxy-2H-pyran (0.987 g, 0.0021 mole) in ethanol (50 ml) was added 20% Pd(OH)$_2$/carbon catalyst (0.31 g). The mixture was heated at reflux with vigorous stirring for four days, at which time tlc (silica gel, 5% acetone-CH$_2$Cl$_2$) indicated the reaction to be essentially complete. Following filtration through a bed of Supercel and evaporation of the solvent there was obtained the title compound (0.83 g) as a crude mixture of ethoxy anomers, as demonstrated by 360 MHz 'H-NMR in DCCl$_3$.

Step D: Preparation of (4R,6S)-(E)-6-[2(4'-Fluoro-3,3',5-trimethyl[1,1'-biphenyl]-2-yl)ethenyl]-3,4,5,6-tetrahydro-2,4-dihydroxy-2H-pyran

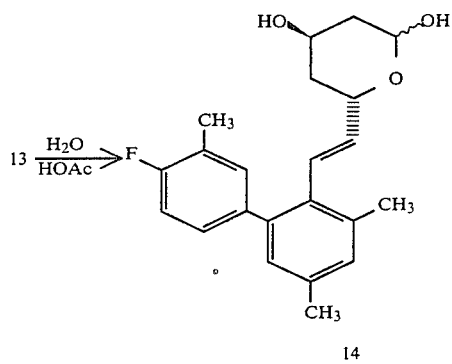

14

To a solution of the crude mixture of anomers, (4R,6S)-(E)-6-[2(4'-fluoro-3,3',5-trimethyl[1,1'-biphenyl]-2-yl)ethenyl]-2-ethoxy-3,4,5,6-tetrahydro-4-hydroxy-2H-pyran (0.83 g, 0.0021 mole) in glacial acetic acid (36 ml) was added water (12 ml). Additional acetic acid (3 ml) was added and the solution allowed to stand for 24 hours at which time tlc (silica gel, 5% acetone-CH$_2$Cl$_2$) indicated the reaction was essentially complete. The reaction mixture was poured into water (800 ml) containing sodium hydroxide (50 g) and extracted with ether (1200 ml). After washing the ether extract with water, drying (MgSO$_4$) and evaporating there was obtained crude lactol product (0.68 g). The crude product was purified by flash chromatography (45 mm id column, 4% actone-CH$_2$Cl$_2$) to give 0.36 g of product which showed a single spot on tlc. 360 MHz H'-NMR in DCCl$_3$ confirmed the presence of two hydroxy anomers in the product.

Step E: Preparation of (+)-(4R,6S)-(E)-6-[2-(4'-Fluoro-3,3',5-trimethyl[1,1'-biphenyl]-2-yl)ethenyl-3,4,5,6-tetrahydro-4-hydroxy-2H-pyran-2-one

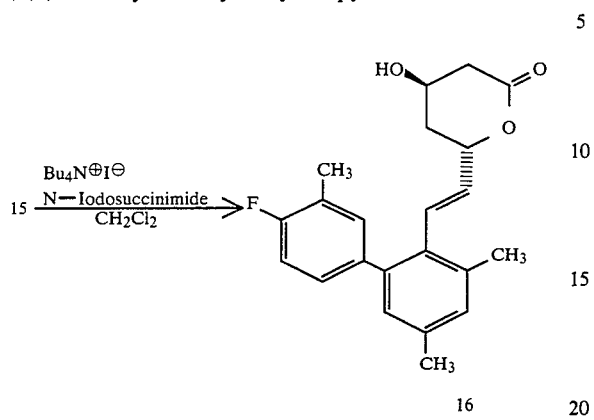

A solution of (4R,6S)-(E)-6-[2-(4'-fluoro-3,3',5-trimethyl[1,1]-biphenyl]-2-yl)ethenyl]-2-ethoxy-3,4,5,6-tetrahydro-4-hydroxy-2H-pyran (0.076 g, 0.00029 mole) in $CH_2Cl_2$ (5 ml) was added to a mixture of N-iodosuccinimide (0.24 g, 0.0011 mole) and tetrabutylammonium iodide (0.079 g) in $CH_2Cl_2$ (35 ml). The mixture was stirred at room temperature for 3 hours. Excess saturated sodium thiosulfate solution was added to decolorize the mixture. Additional $CH_2Cl_2$ was added and the organic layer separated, washed well with $H_2O$, and dried ($MgSO_4$). Evaporation gave crude lactone (0.041 g), which was purified by preparative tlc (silica gel, 2000μ, 7% acetone-$CH_2Cl_2$) to give pure title product (0.033 g). 'H-NMR ($CDCl_3$) studies with and without europium chiral NMR shift reagent, demonstrate the product to be identical with the biologically active diastereomer prepared by a process requiring chemical resolution.

Employing the procedure substantially as described in Example 2, but substituting for the (4'-fluoro-3,3',5-trimethyl-[1,1'-biphenyl[-2-yl-methyl)phenyl sulfoxide used in Step A thereof, an equimolecular amount of each of the $R^1$, $R^2$, $R^3$-benzyl phenyl sulfoxides described in Table I, there is produced the respective tetrahydro-2H-pyran-2-ones, also described in Table I.

TABLE I

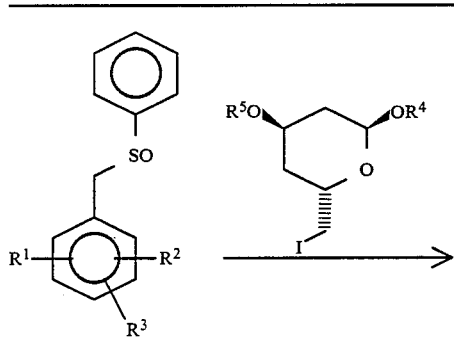

TABLE I-continued

| $R^1$ | 2-$R^2$ | 4-$R^3$ |
|---|---|---|
| F—⟨⟩— | Cl | Cl |
| CH₃<br>F—⟨⟩— | Cl | Cl |
| Cl<br>Cl—⟨⟩— | CH₃ | CH₃ |
| F—⟨⟩— | CH₃ | CH₃ |
| CH₃<br>F—⟨⟩— | Cl | CH₃ |
| CH₃<br>F—⟨⟩—<br>CH₃ | CH₃ | CH₃ |
| CH₃<br>⟨⟩—<br>CH₃ | Cl | Cl |
| CH₃<br>⟨⟩—<br>CH₃ | CH₃ | CH₃ |
| F—⟨⟩—CH₂O— | CH₃ | CH₃ |
| F—⟨⟩—CH₂O— | Cl | Cl |
| H | Cl | Cl |

EXAMPLE 3

(4R,6S) 6-[2-(2,4-dichlorophenyl)ethyl]-4-hydroxy-3,4,5,6-tetrahydro-2H-pyran-2-one Step A: Preparation of 1-(2,4-dichlorophenyl)-2-(4(R)-benzyloxy-2(R)-methoxy-3,4,5,6-tetrahydro-2H-pyran-6(S)-yl)ethyl phenyl sulfone

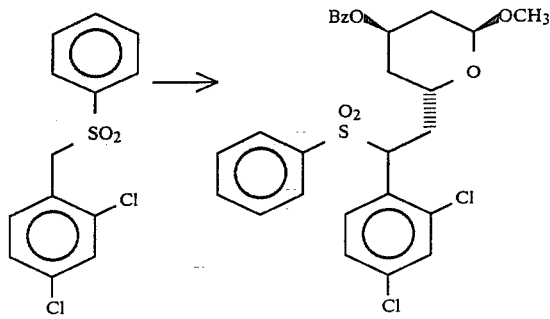

To a stirred suspension of sodium hydride (0.030 g of 50% NaH in mineral oil) in dry DMF (0.5 ml) under nitrogen is added 2,4-dichlorobenzyl phenyl sulfone (0.18 g; 0.6 mmole) as the crystalline solid all at once. The reaction mixture is stirred at room temperature under nitrogen under hydrogen evolution ceases (50 min.) A solution of (2R,4R,6S)-4-benzyloxy-6-iodomethyl-2-methoxy-3,4,5,6-tetrahydro-2H-pyran (0.109 g; 0.3 mmole) in dry DMF (0.4 ml) is added by syringe through a septum. The reaction is stirred for 2.5 hours at room temperature and then partitioned between ether (100 ml) and water (20 ml). The ether layer is extracted with water (4×20 ml), dried (MgSO4), filtered, and the solvent evaporated in vacuo to leave 0.24 g of crude product. Flash chromatography of this product on silica gel with a 30 mm×130 mm column, eluting with 2% (by volume) acetone in methylene chloride, gives 40 mg of the major diastereoisomer and 10 mg of the minor diastereoisomer and 60 mg of a mixture of the two with a total of 110 mg of 1-(2,4-dichlorophenyl)-2-(4(R)-benzyloxy-2(R)-methoxy-3,4,5,6-tetra-hydro-2H-pyran-6(S)-yl)ethyl phenyl sulfone.

pmr (DCCl3) 1.3–1.98 (4H, m); 2.3 (2H, m); 3.08 (3H, S); 3.48–3.94 (2H, 2m) 4.5 (2H, q); 4.64 (1H, m); 5.2 (1H, dd); 7.2–7.7 (13H, m).

Step B: Preparation of 4(R)-Benzyloxy-6(S)-[2-(2,4-dichlorophenyl)ethyl]-2(R)-methoxy-3,4,5,6-tetrahydro-2H-pyran

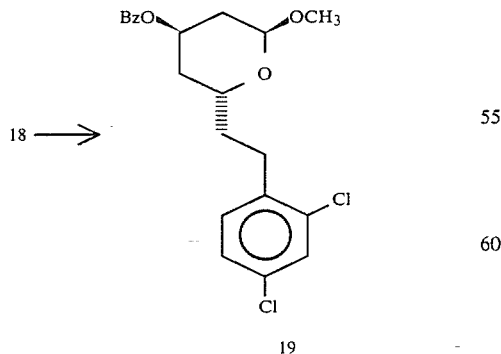

To a mixture of 1-(2,4-dichlorophenyl)-2-(4(R)-benzyloxy-2(R)-methoxy-3,4,5,6-tetrahydro-2H-pyran-6(S)-yl)ethyl phenyl sulfone (0.06 g, 0.11 mmole) and anhydrous disodium phosphate (0.065 g, 0.45 mmoles) in dry methanol (5 ml) was added pulverized 5% sodium amalgam (0.2 g). The mixture was stirred at room temperature for twenty hours, during which time an additional 0.4 g of 5% sodium amalgam was added in three portions. The reaction mixture was poured into water and extracted with ether. The ether solution was dried (MgSO4), filtered, and the solvent evaporated in vacuo to give the title compound as a colorless viscous oil (0.04 g); 'H NMR (CDCl3) δ 1.53 (1H, ddd), 1.58–1.88 (4H, m), 2.06 (1H, m), 2.70 (1H, ddd), 2.95 (1H, ddd), 3.42 (3H, s), 3.76 (1H, p), 4.16 (1H, d), 4.52 (1H, d), 4.65 (1H, d), 4.78 (1H, dd), 7.13–7.40 (8H, m).

Step C: Preparation of 6(S)-[2-(2,4-dichlorophenyl)ethyl]-2(R)-methoxy-4(R)-hydroxy-3,4,5,6-tetrahydro-2H-pyran

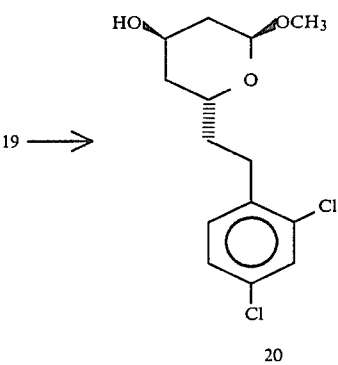

4(R)-Benzyloxy-6(S)-[2-(2,4-dichlorophenyl)ethyl]-2(R)-methoxy-3,4,5,6-tetrahydro-2H-pyran (0.395 g, 1 mmol) is dissolved in ethanol 25 ml and Pd (OH)2 (Pearlman) (10 mg) is added and the stirred reaction mixture hydrogenated until one mmole of H2 is taken up, the reaction is purged of hydrogen, filtered, and the solvent evaporated at reduced pressure to leave 6(S)-[2-(2,4-dichlorophenyl)ethyl]-2-(R)-methoxy-4R-hydroxy-3,4,5,6-tetrahydro-2H-pyran.

Alternate Step C: Preparation of 6(S)-[2-(2,4-dichlorophenyl)-ethyl]-2-ethoxy-4R-hydroxy-3,4,5,6-tetrahydro-2H-pyran

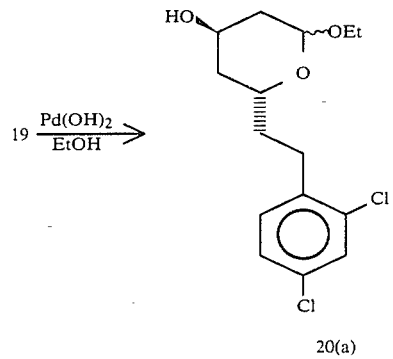

4(R)-Benzyloxy-6-(S)-[2-(2,4-dichlorophenyl)ethyl]-2(R)-methoxy-3,4,5,6-tetrahydro-2H-pyran (0.395 g, 1 mmole) is dissolved in ethanol (30 mL) and palladium hydroxide on carbon (Pearlman catalyst) (1.25 g) is added and the mixture stirred and refluxed for 20 hours, when tlc (5% acetone in CH2Cl2) shows the reaction to be complete, the reaction is cooled to room temperature, the catalyst filtered and the solvent evaporated in vacuo to leave a mixture of anomers, 6(S)-[2-(2,4-dichlorophenyl)ethyl]-2-ethoxy-4(R)-hydroxy-3,4,5,6-tetrahydro-2H-pyran. This product is used without purification in the next step.

Step D: Preparation of 6(S)-[2-(2,4-dichlorophenyl)ethyl]-2-hydroxy-4(R)hydroxy-3,4,5,6-tetrahydro-2H-pyran-2-one

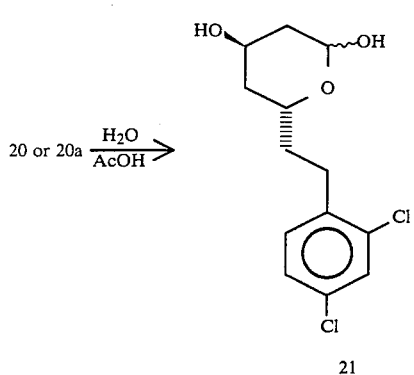

6(S)-[2-(2,4-dichlorophenyl)-ethyl]-2-ethoxy-4(R)-hydroxy-3,4,5,6-tetrahydro-2H-pyran (0.305 g, 1 mmole) is dissolved in 80% aqueous acetic acid (5 ml) and heated at 70° to 80° for 2 hours. When tlc shows that, the reaction is complete, (if necessary the reaction may be heated at 90° bath temp. for 2 hours). The reaction solution is dissolved in ether and extracted with water, then dilute sodium hydroxide, until washings are basic, and then with water. The ether layer is dried (MgSO4), filtered, and the solvent is evaporated in vacuo to leave 6(S)-[2-(2,4-dichlorophenyl)ethyl]-2-hydroxy-4(R)-hydroxy-3,4,5,6-tetrahydro-2H-pyran.

Step E: Preparation of (4R,6S) 6-[2-(2,4-dichlorophenyl)ethyl]-4-hydroxy-3,4,5,6-tetrahydro-2H-pyran-2-one

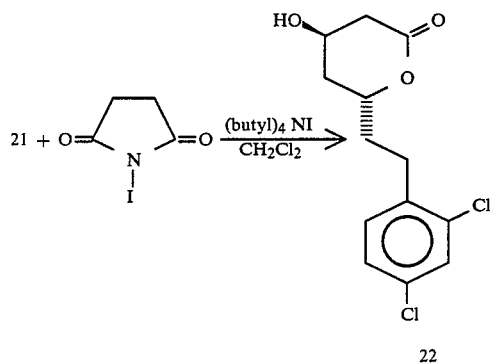

6(S)-[2-(2,4-dichlorophenyl)ethyl]-2-hydroxy-4(R)-hydroxy-3,4,5,6-tetrahydro-2H-pyran (0.291 g, 1 mmole) is dissolved in methylene chloride (10 ml) and added to a well stirred mixture of N-iodosuccinimide (1.14 g, 5 mmoles) and tetrabutyl ammonium iodide (0.4 g, 1 mmole) in methylene chloride (20 ml). The red brown mixture is stirred at room temperature for 2 hours. After tlc shows reaction complete, a saturated solution of sodium thiosulfate (30 ml) is added and the mixture is stirred vigorously until the mixture is nearly colorless. The mixture is diluted with ether and extracted with water, dried (MgSO4), and the solvent evaporated in vacuo to give (4R,6S) 6[2-(2,4-dichlorophenylethyl]-4-hydroxy-3,4,5,6-tetrahydro-2H-pyran-2-one.

Employing the procedure substantially as described in Example 3, but substituting for the 2,4-dichlorobenzyl phenyl sulfone(17) used in Step A thereof, an equimolecular amount of the $R^1$, $R^2$, $R^3$-benzyl phenyl sulfones described in Table II, there are produced the respective tetrahydro-2H-pyran-2-ones, also described in Table II.

TABLE II

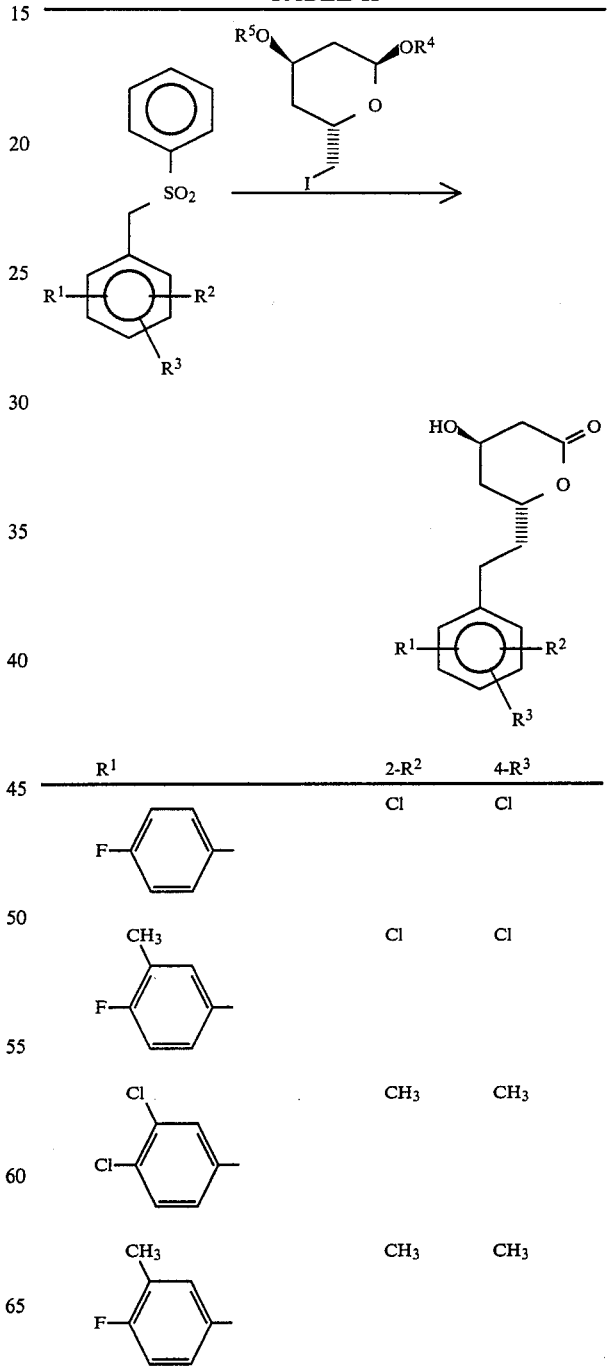

| $R^1$ | 2-$R^2$ | 4-$R^3$ |
|---|---|---|
| F—⟨phenyl⟩— | Cl | Cl |
| CH3, F—⟨phenyl⟩— | Cl | Cl |
| Cl, Cl—⟨phenyl⟩— | CH3 | CH3 |
| CH3, F—⟨phenyl⟩— | CH3 | CH3 |

TABLE II-continued

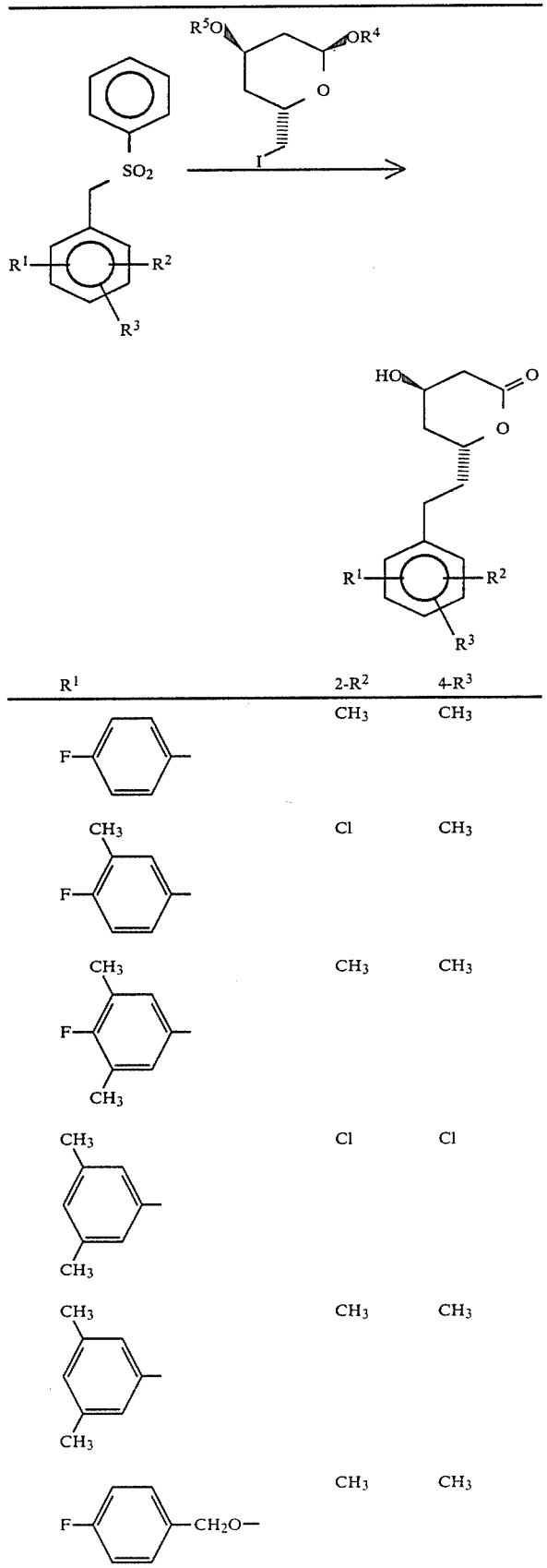

| $R^1$ | 2-$R^2$ | 4-$R^3$ |
|---|---|---|
|  | CH$_3$ | CH$_3$ |
| F—⟨phenyl⟩— |  |  |
| CH$_3$-⟨phenyl, F⟩— | Cl | CH$_3$ |
| CH$_3$,CH$_3$-⟨phenyl, F⟩— | CH$_3$ | CH$_3$ |
| CH$_3$,CH$_3$-⟨phenyl⟩— | Cl | Cl |
| CH$_3$,CH$_3$-⟨phenyl⟩— | CH$_3$ | CH$_3$ |
| F-⟨phenyl⟩—CH$_2$O— | CH$_3$ | CH$_3$ |

TABLE II-continued

| $R^1$ | 2-$R^2$ | 4-$R^3$ |
|---|---|---|
|  | Cl | Cl |
| F-⟨phenyl⟩—CH$_2$O— |  |  |

What is claimed is:

1. A process for preparing the compound of structural formula:

(I)

wherein:
$R^2$ and $R^3$ are independently chloro or $C_{1-3}$alkyl; and
$R^1$ is (1)

F-⟨phenyl⟩—CH$_2$O—, or

-continued

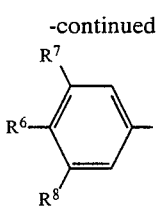 (2)

wherein
R[6] is hydrogen, fluoro- or chloro, and R[7] and R[8] are independently hydrogen, chloro or C$_{1-3}$alkyl; which comprises the steps of:

(A) treating a compound of structural formula:

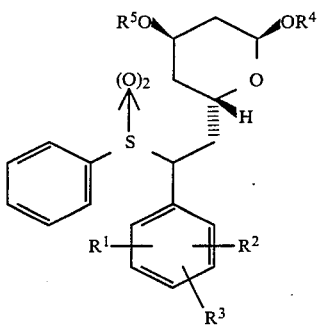 VII wherein R[4] is C$_{1-3}$alkyl; R[5] is benzyl, or 4-methoxybenzyl; with sodium amalgam at 20° to 40° C. for 0.25 to 6 hours to produce the compound of formula:

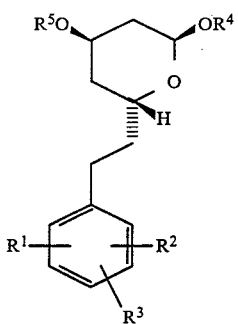 VIII (B) followed by treatment with hydrogen in the presence of a hydrogenation catalyst to remove the R[5] group followed by treatment with aqueous acetic acid to produce the compound of structure X

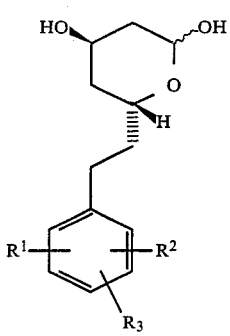 X (C) followed by treatment with an oxidizing agent to produce the compound of formula

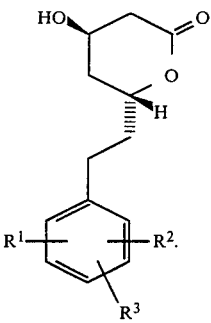

2. The process of claim 1 which comprises treating the compound of structural formula:

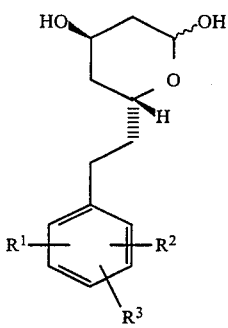

with N-iodosuccinimide and tetra-n-butylammonium iodide in an inert solvent to produce the compound of structural formula:

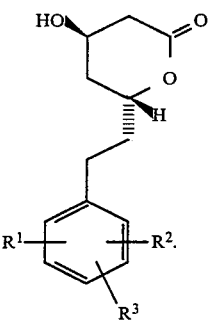

3. The process of claim 1 or 2 for the preparation of the compound of structural formula:

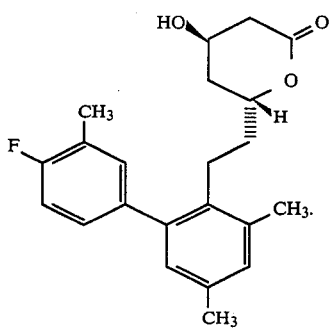

* * * * *